(12) United States Patent
Dobosz

(10) Patent No.: US 7,385,498 B2
(45) Date of Patent: Jun. 10, 2008

(54) WRISTBAND READER APPARATUS FOR HUMAN-IMPLANTED RADIO FREQUENCY IDENTIFICATION DEVICE

(75) Inventor: Paul J. Dobosz, Noblesville, IN (US)

(73) Assignee: Delphi Technologies, Inc., Troy, MI (US)

(*) Notice: Subject to any disclaimer, the term of this patent is extended or adjusted under 35 U.S.C. 154(b) by 224 days.

(21) Appl. No.: 11/437,161

(22) Filed: May 19, 2006

(65) Prior Publication Data

US 2007/0268144 A1 Nov. 22, 2007

(51) Int. Cl.
*G08B 1/08* (2006.01)

(52) U.S. Cl. .............................. 340/539.12; 340/572.8; 340/539.1; 340/572.1; 340/573.1

(58) Field of Classification Search ........... 340/539.12, 340/539.11, 539.1, 539.13, 539.23, 572.8, 340/572.1, 573.1
See application file for complete search history.

(56) References Cited

U.S. PATENT DOCUMENTS 6,078,803 A * 6/2000 Fernandez Martinez .... 455/349
6,098,877 A * 8/2000 Barkan et al. ................. 235/25
6,585,763 B1 * 7/2003 Keilman et al. ........... 623/1.42

OTHER PUBLICATIONS

U.S. Appl. No. 11/311,721, filed Dec. 19, 2005, Paul J. Dobosz.

* cited by examiner

*Primary Examiner*—Daryl C Pope
(74) *Attorney, Agent, or Firm*—Jimmy L. Funke

(57) ABSTRACT

A reader apparatus for an RFID-implanted human user is incorporated into a wristband such as a bracelet or a watchstrap worn by the user. The RFID device is subcutaneously implanted in the vicinity of the user's wrist, ensuring close proximity of the reader apparatus to the RFID device to support reliable near-field RF communications at low power levels. The wristband includes a reader coil having a plurality of turns, a reader circuit, and a rechargeable battery for powering the reader circuit. The same reader coil is used to simplify recharging of the battery by inductively coupling the reader coil to a charging coil disposed in a small charging stand or storage case. In watch strap applications, the reader circuitry and battery are disposed in a watch case affixed to the strap, and the watch case includes an alphanumeric display for communicating information from the RFID device to the user.

6 Claims, 3 Drawing Sheets

WRISTBAND READER APPARATUS FOR HUMAN-IMPLANTED RADIO FREQUENCY IDENTIFICATION DEVICE

TECHNICAL FIELD

The present invention relates to apparatus for periodically reading data stored or acquired by a human-implanted passive radio frequency identification (RFID) device, and more particularly to a reader apparatus incorporated into a wristband worn by the human.

BACKGROUND OF THE INVENTION

Although passive radio-frequency identification (RFID) devices have been approved for subcutaneous implanting in human beings, it can be difficult to design a battery operated bodily worn reader apparatus that is capable of reliably communicating with an implanted device under all conditions. The difficulties arise due to variations in clothing, skin thickness and proximity of the reader to the implanted device, for example. A practical reader apparatus must be small in size and low in power consumption, and this can only be achieved if the reader apparatus is maintained in close proximity to the implanted device. Accordingly, what is needed is a reader apparatus that is both practical and convenient for an RFID-implanted person to wear and maintain.

SUMMARY OF THE INVENTION

The present invention is directed to an improved reader apparatus for an RFID-implanted human user, the reader apparatus being incorporated into a wristband such as a bracelet or a watchstrap worn by the user. The RFID device is subcutaneously implanted in the vicinity of the user's wrist, ensuring close proximity of the reader apparatus to the RFID device to support reliable near-field RF communications at low power levels. The wristband supports a reader coil having a plurality of turns, a reader circuit, and a rechargeable battery for powering the reader circuit. The same reader coil is used to simplify recharging of the battery by inductively coupling the reader coil to a charging coil disposed in a small charging stand or storage case. In watch strap applications, the reader circuitry and battery may be disposed in a watchcase affixed to the strap, and the watchcase may include an alphanumeric display for communicating information from the RFID device to the user.

DESCRIPTION OF THE PREFERRED EMBODIMENT

Figure 1:
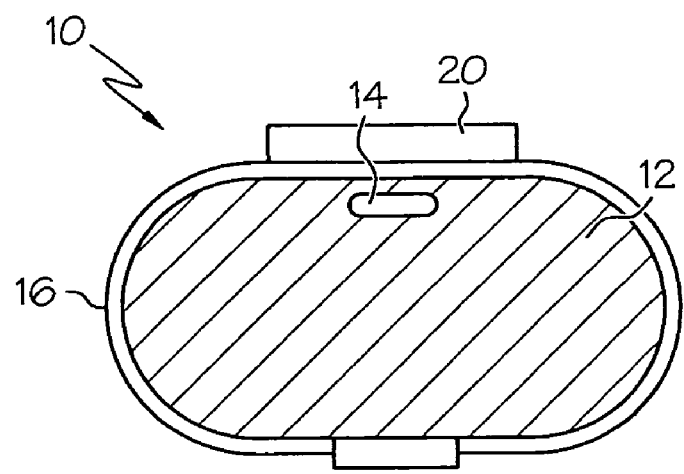
FIG. 1 is a diagram of a RFID-implanted human wrist and a wristband reader apparatus according to the present invention.
Figure 2:
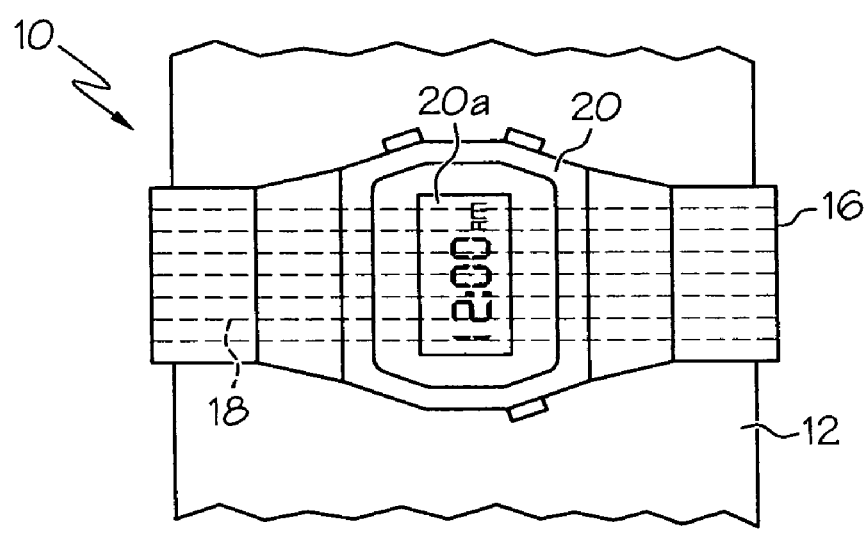
FIG. 2 is a diagram of a wristband and watchcase according to the present invention.

Referring to FIGS. 1-2, the reference numeral 10 generally designates a wristband reader apparatus in accordance with this invention in the form of a conventional-appearing wristwatch worn on a person's wrist or forearm 12. The partial sectional view of FIG. 1 illustrates a human-implantable RFID pellet 14 subcutaneously implanted in the forearm 12. The reader apparatus 10 includes at least a wristband 16 supporting a multi-turn reader coil 18, shown in phantom in FIG. 2. The wristband 16 by nature is maintained in very close proximity to the implanted RFID pellet 14 so that the reader coil 18 physically encircles the wrist 12 in the immediate vicinity of RFID pellet 14. Reader circuitry, display components, and circuitry for wireless transfer of data from the reader apparatus 10 to a communications network may be embedded in or affixed to the wristband 16 itself, but are preferably mounted in a compartment carried by the wristband 16. In the illustrated embodiment, for example, the reader circuitry and display components are housed in a watchcase 20 affixed to the wristband 16, and the terminals of reader coil 18 are electrically linked to the reader circuitry through the watchcase 20. The reader display 20a is mounted in the face of the watchcase 20 for easy viewing of information stored in or acquired by RFID pellet 14, and may double as a conventional time/date display, reader status display, and battery state of charge indicator, if desired.

Figure 3:
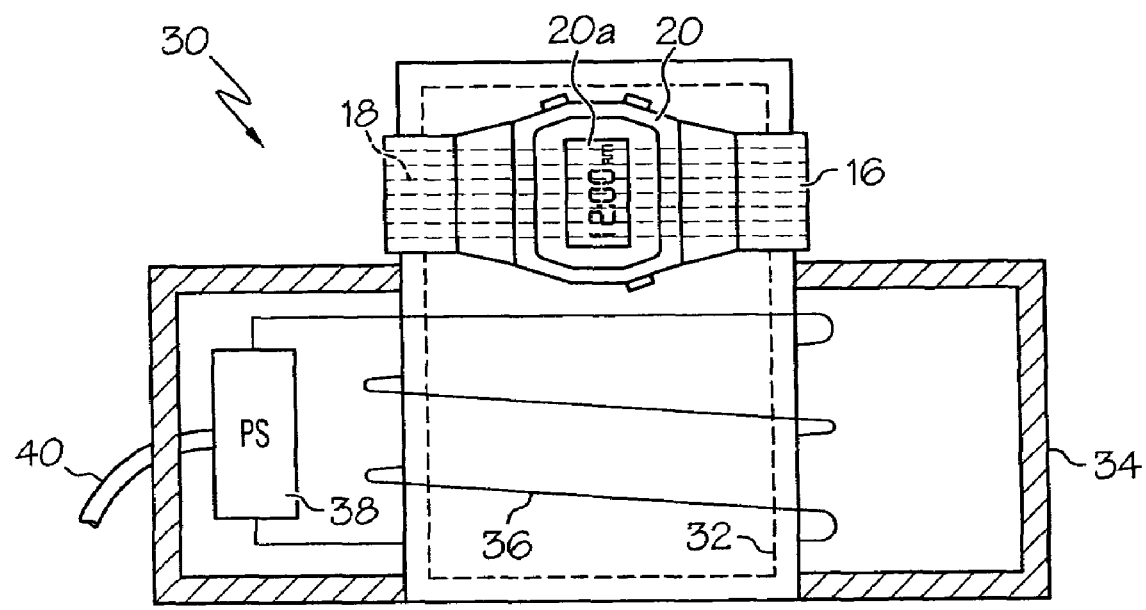
FIG. 3 is a block diagram of a battery charger for the wristband reader apparatus of FIGS. 1-2.

As described below in reference to FIG. 4, a rechargeable battery 62 mounted in the watchcase 20 powers the reader circuitry and display 20a. Referring to FIG. 3, a remote charging apparatus 30 is provided for recharging the battery 62 without having to remove it from watchcase 20. The charging apparatus 30 includes a ferromagnetic post 32 coated with a non-magnetic insulation material and mounted in a housing 34, where the post 32 protrudes from the housing 34 to form a docking platform for the wristband 16. During battery charging, the wristband 16 is removed from the user's wrist 12 and positioned around the exposed portion of the post 32 as illustrated in FIG. 3. The charging apparatus 30 additionally includes an internal charging coil 36 that encircles the post 32 within the housing 34, and a power supply (PS) 38 that operates off an AC line cord 40 to energize the charging coil 36 with high frequency (100 kHz, for example) alternating current. The ferromagnetic post 32 magnetically couples the charging coil 38 to the reader coil 18 embedded in wristband 16, and circuitry in the watchcase 20 rectifies the current induced in reader coil 18 to supply charging current to battery 62. Thus, the reader coil 18 is used as an antenna for RF communications when the wristband 16 is worn on the user's wrist 12, and as a charging current collector when removed from the wrist 12 and positioned on the charging apparatus 30.

Figure 4:
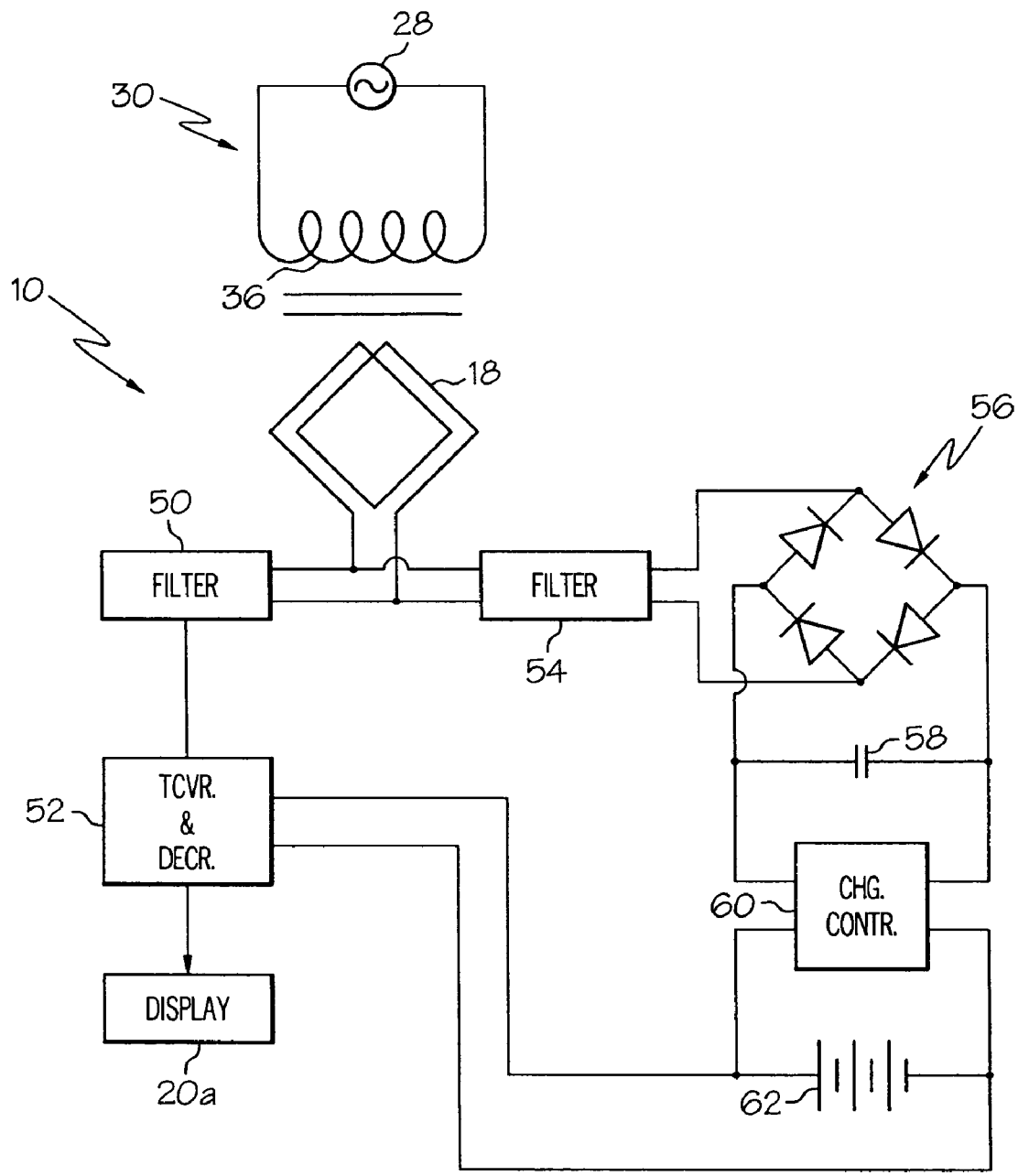
FIG. 4 is a block diagram of the wristband reader apparatus and battery charger of FIGS. 1-3.

FIG. 4 is a schematic diagram of the wristband reader apparatus 10 and charging apparatus 30. In respect to charging apparatus 30, the charging coil 36 is depicted as an inductor and the power supply 38 is depicted as an AC power source. The reader coil 18 is depicted as a multi-turn coil magnetically coupled to the charging coil 36.

When the wristband reader apparatus 10 is disposed on the post 32 of charging apparatus 30 as shown in FIG. 3 and power supply 38 is activated to excite charging coil 36 with high frequency alternating current, the alternating current inductively coupled into reader coil 18 passes un-attenuated through bandpass filter 54 and is converted to direct current by full-wave rectifier 56 and filter capacitor 58 for application to charging control circuit 60. Charging control circuit 60 controls the application of the direct current to rechargeable battery 62 to quickly charge the battery 62 and then maintain it in a fully charged state.

When the wristband reader apparatus 10 is removed from the charging apparatus 30 and place on the user's wrist 12 as shown in FIGS. 1-2, the charging circuit components described in the preceding paragraph are no longer active, and battery 62 supplies operating power to an RF transceiver and decoder circuit 52. The circuit 52 is coupled to reader coil 18 via bandpass filter 50, and operates in half-duplex fashion to periodically excite reader coil 18 and decode data received from the user-embedded RFID pellet 14. This information may include, for example, the user's identity and medical conditions, as well as biometric information such as the user's body temperature, heart rate and blood pressure. The bandpass filter 50 is resonant at the RFID excitation frequency so as to isolate RF transceiver and decoder circuit 52 from battery charging current when the reader apparatus 10 is positioned on charging apparatus 30 for charging battery 62. The RF transceiver and decoder circuit 52 is also coupled to the watchcase display 20a, and activates the display 20a to communicate the decoded information to the user, either automatically or in response to depression of one or more of the buttons at the periphery of watchcase 20. The watchcase may also include an alarm that is activated by circuit 52 when a monitored parameter such as the user's body temperature exceeds a preset threshold.

In summary, the present invention provides a practical and convenient way of utilizing a human-implanted RFID pellet 14. Close and consistent proximity of the reader coil 18 to the pellet 14 is ensured, allowing the reader circuitry to be small in size and low in power consumption. Using the reader coil 18 for both RF communications during use and inductive energy transfer during battery charging enhances user convenience while minimizing cost. While the present invention has been described with respect to the illustrated embodiment, it is recognized that numerous modifications and variations in addition to those mentioned herein will occur to those skilled in the art. For example, the watchcase 20 may additionally include circuitry for transmitting data to a remote receiver using common wireless communication protocols such as infrared, Bluetooth, Zigbee, 802.11a, b, g, or any other appropriate and convenient means of wireless communication. Accordingly, it is intended that the invention not be limited to the disclosed embodiment, but that it have the full scope permitted by the language of the following claims.

The invention claimed is:

1. Apparatus for communicating with a passive radio frequency device implanted in a forearm of a human subject, comprising:

a wristband encircling the forearm of the subject in proximity to the implanted radio frequency device during a communication mode of operation;

a multi-turn reader coil embedded in said wristband;

reader circuitry supported by said wristband and coupled to said reader coil for communicating with the implanted radio frequency device and acquiring data therefrom;

a rechargeable battery supported by said wristband for powering said reader circuitry; and a charging platform on which said wristband is positioned during a charging mode of operation, said charging platform including a charging coil inductively coupled to said reader coil to provide charging current to said rechargeable battery during said charging mode of operation.

2. The apparatus of claim 1, further comprising:

a watchcase secured to said wristband, and housing said reader circuitry and said rechargeable battery, said watchcase including a digital display for displaying data acquired by said reader circuitry.

3. The apparatus of claim 1, where said charging platform comprises:

a ferromagnetic post on which said charging coil is wound, and a power supply for exciting said charging coil with alternating current, said wristband being positioned to encircle said ferromagnetic post during said charging mode of operation.

4. The apparatus of claim 3, where said charging platform further comprises a housing that supports said ferromagnetic post, and where said ferromagnetic post protrudes from said housing to define a docking station for said wristband during said charging mode of operation.

5. The apparatus of claim 1, where said reader circuitry includes conversion circuitry for converting current inductively coupled into said reader coil during said charging mode of operation into charging current for said rechargeable battery.

6. The apparatus of claim 1, where said reader circuitry includes wireless communication circuitry to allow the data acquired from said implanted radio frequency device to be wirelessly monitored at a location remote from said subject.

* * * * *